United States Patent [19]
Yoches et al.

[11] Patent Number: 5,400,799
[45] Date of Patent: Mar. 28, 1995

[54] METHOD OF MONITORING UTERINE ACTIVITY IN VETERINARY OBSTETRICS

[76] Inventors: Cheri C. Yoches, 3665 Cherry Creek Dr. N., Ste. 1, Denver, Colo. 80209; Karen C. Snyder, 9111 W. 38th Ave., Wheet Ridge, Colo. 80033

[21] Appl. No.: 180,033

[22] Filed: Jan. 11, 1994

[51] Int. Cl.6 .............................................. A61B 5/103
[52] U.S. Cl. ................................................... 128/778
[58] Field of Search ................. 128/774, 775, 778, 782

[56] References Cited

U.S. PATENT DOCUMENTS

| | | | |
|---|---|---|---|
| 4,232,686 | 11/1980 | Kammlade | 128/775 |
| 4,707,685 | 11/1987 | Carrier et al. | 128/775 |
| 5,042,503 | 8/1991 | Torok et al. | 128/778 |
| 5,070,888 | 12/1991 | Hon et al. | 128/778 |
| 5,205,296 | 4/1993 | Dukes et al. | 128/775 |
| 5,301,680 | 4/1994 | Rosenberg | 128/778 |

OTHER PUBLICATIONS

"Uterine Electromyographic Activity In Horse Mares As Measured By Radiotelemetry," Theriogenology, Mar., 1991, vol. 35, No. 3, pp. 591–601.

*Primary Examiner*—Max Hindenburg

[57] ABSTRACT

A method is disclosed for monitoring the uterine activity of an animal. An electronic sensor is placed over the animal's abdomen and the detected signals are sent to a monitoring device which records the signals, for example, for display or transmission.

6 Claims, 4 Drawing Sheets

METHOD OF MONITORING UTERINE ACTIVITY IN VETERINARY OBSTETRICS

I. BACKGROUND OF THE INVENTION

The present invention relates to the field of uterine monitoring for veterinary purposes and, more particularly, to such monitoring using low cost electronic devices.

All mammals that deliver live offspring carry their fetus inside a uterus. As it grows and stretches to accommodate the fetus, the uterus periodically contracts. Studies of human pregnancies have shown that the frequency of these contractions will increase 24 to 48 hours prior to labor and delivery. Labor occurs when regular contractions dilate the cervix, the opening to the uterus, to allow delivery of the offspring through the birth canal.

The use of electronic devices to monitor human labor and delivery has been popular since the 1970's. Obstetricians often monitor the uterine activity of women to predict the onset of labor, both term and preterm, to ensure that proper precautions are initiated. Home monitoring of uterine activity has become increasingly popular, and is now advocated by many obstetricians and perinatologists using the monitor to detect premature labor.

Uterine monitoring uses a tococdynometer to sense uterine irritability (a low amplitude, high frequency pattern) and uterine contractions. The tococdynometer is placed outside a woman's body near the uterus.

In the 1980's, the design of the tococdynometer improved sufficiently to allow patients at risk of preterm delivery to have their uterine activity monitored at home. The current home monitoring devices are much more sensitive to the detection of uterine activity than prior equipment used in a clinical setting to monitor term gestation. In fact, monitoring devices can now detect uterine activity as early as sixteen weeks into gestation.

To date, uterine monitoring has been limited to humans. One reason may be that delivery of human offspring takes so much longer delivery of other mammal offspring. For example, a typical human delivery averages twelve to fourteen hours from the onset of labor. A cow, on the other hand, calves in around three hours.

Veterinarians, animal owners, and other animal health care providers could benefit from monitoring uterine activity in animals to permit timely response, management, and treatment of animals during gestation, labor and delivery. The ability to herald the onset of labor before the animal exhibits the typical signs allows quicker response and preparedness on the part of the owner, caretaker, or veterinarian. Such uterine monitoring can be especially beneficial for animals in the growing speciality of planned animal reproduction because certain artificial inseminations are sufficiently valuable to warrant close evaluation of the subsequent pregnancy and general prenatal health of the animal.

There are many other conditions which threaten the viability of the mammal offspring that may benefit from uterine monitoring. These conditions include inducing or augmenting labor, multiple gestation, reproductive-/infectious disease, a history of premature delivery of the offspring, uterine or pelvic abnormality.

II. SUMMARY OF THE INVENTION

Accordingly, it is desirable to monitor uterine activity in mammals to track gestation and delivery. It is especially desirable to monitor such activity method outside of a clinic.

It is also desirable to detect the onset of early labor as well as labor in its active stage.

Additional desires and advantages of the invention will be set forth in part in the description which follows, and in part will be obvious from the description, or may be learned by practice of the invention. The desires and advantages of the invention will be realized and attained by means of the elements and combinations particularly pointed out in the appended claims.

To achieve the objects and in accordance with the purpose of the invention, as embodied and broadly described herein, the invention comprises a method of monitoring uterine activity in an animal which comprises the steps of positioning a sensor for uterine activity on an animal such that the sensor will detect uterine activity of the animal; connecting the sensor to an electronic device for recording the uterine activity of the animal; and periodically recording the uterine activity of the animal using the electronic device.

Both the foregoing general description and the following detailed description are exemplary and explanatory only and do not restrict the invention as claimed.

The accompanying drawings, which are incorporated in and constitute a part of this specification, illustrate one embodiment of the invention and, together with the description, serve to explain the principles of the invention.

III. BRIEF DESCRIPTION OF THE DRAWINGS

IV. DESCRIPTION OF THE PREFERRED IMPLEMENTATION

Reference will now be made in detail to the preferred implementation of the invention illustrated in the accompanying drawings. Wherever possible, the same reference numbers will be used throughout the drawings to refer to the same or similar parts.

The invention involves the use of an electronic uterine activity monitoring device to detect uterine activity in mammals, such as dogs, livestock, horses, exotics, and endangered animals. The method is not only useful for assisting delivery, but also in gathering data to determine the onset of labor and delivery and predict premature labor and delivery. It may also be useful in managing the induction of the active labor phase.

Figure 1A:
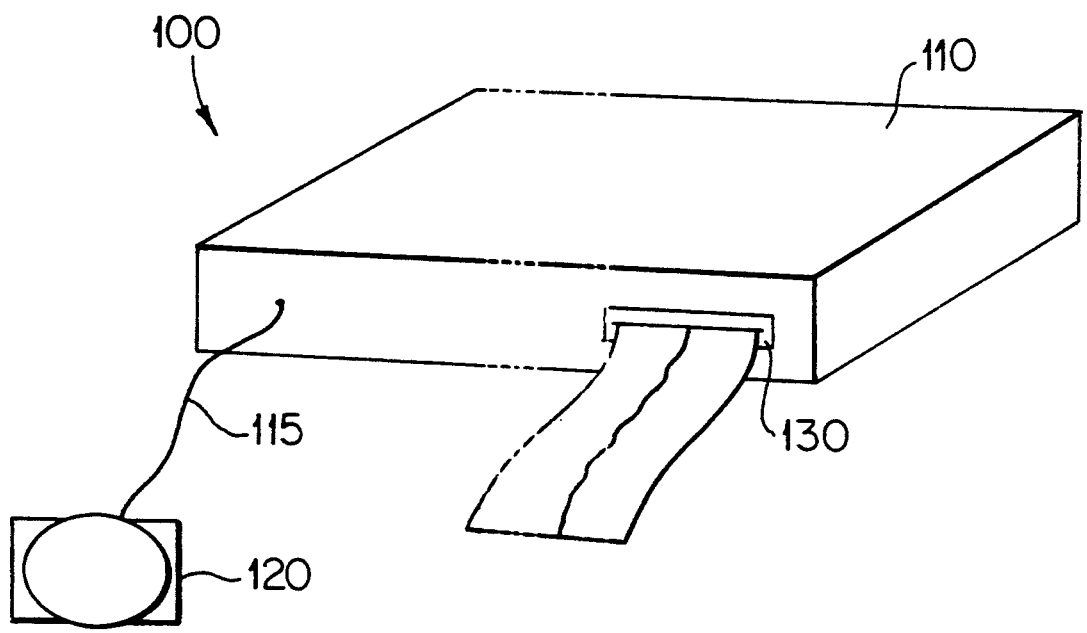
FIGS. 1A and 1B show the front and back views, respectively, of a typical uterine monitoring device that can be used with this invention.
Figure 1B:
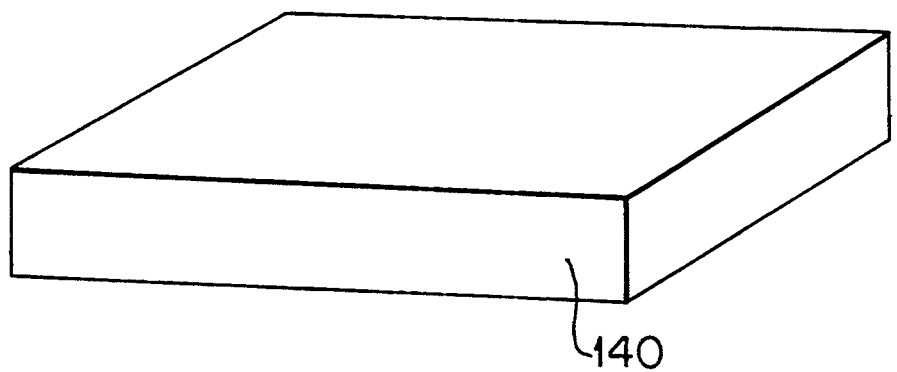

FIGS. 1A and 1B show the front and back views, respectively, of a monitoring device 100. Monitoring device 100 includes a monitor 110 connected to a sensor 120 via a cord 115. Sensor 120, which is known as a tococdynometer, detects uterine contractions using a pressure-sensitive sensor that electromagnetically creates an electric signal. Cord 115 carries that electric signal to monitor 110. One example of sensor 120 is a Smyth-Guard Ring. Another is a microprocessor-driven sensor to perceive changes in interabdominal pressure.

Cord 115 is not required if sensor 120 is capable of transmitting a signal to monitor 110. A cordless sensor 120 could be worn continuously by the animal. The Smyth-Guard Ring or the interabdominal pressure sensor may be used in such an application.

In addition, the microprocessor in an interabdominal pressure sensor could also be programmed to alarm if the sensed signal deviated significantly form a baseline trace. This alarm could also be transmitted through conventional means to a designated area, such as a clinic, a barn, or a house, or could signal a paging device or use cellular telephone technology.

Monitor 110 processes the detected signal for recording, display, transmission, or any other desired activity. Monitor 110 can include a strip chart recorder 130 or some other display device to show the detected signals in real time. Monitor 110 also may include a modem 140 to transmit the recorded signals to a remote facility over a standard telephone line, and to receive data from such a facility. Communication with a remote facility is especially useful for gathering data or seeking consultation.

Monitor 110 could be used to process the signals from several sensors especially if they are cordless. In such an arrangement, the display connected to monitor 110 could show traces from several animals, or could store data for later analysis.

Monitoring device 100 should be light enough to carry into the field, yet durable enough to withstand use with animals. Although some modifications may be desirable to adapt human uterine monitoring devices to animal use, such modifications should not change the basic operation of uterine monitoring.

Figure 2:
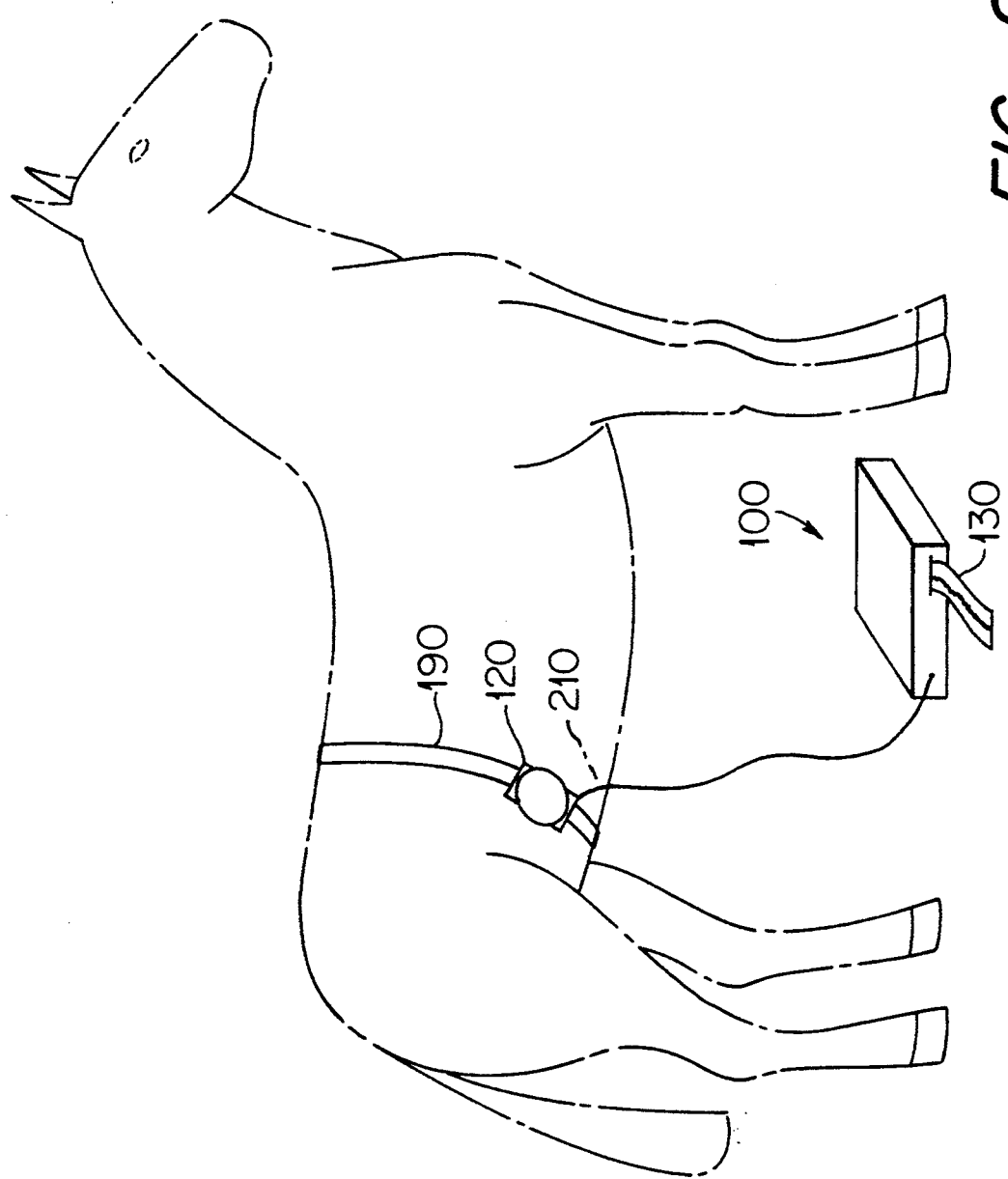
FIG. 2 shows the application of the device in FIGS. 1A and 1B to a horse.

FIG. 2 shows the use of monitoring device 100 with a pregnant horse. As FIG. 2 shows, sensor 120 of monitoring device 100 is placed on the lower abdomen 210 over the uterus and held in place with belt 190. To ensure the proper placement, the caregiver should be educated on proper sensor placement. In addition, strip chart recorder 130 can be used to indicate when a sufficiently strong signal has been detected.

Figure 3:
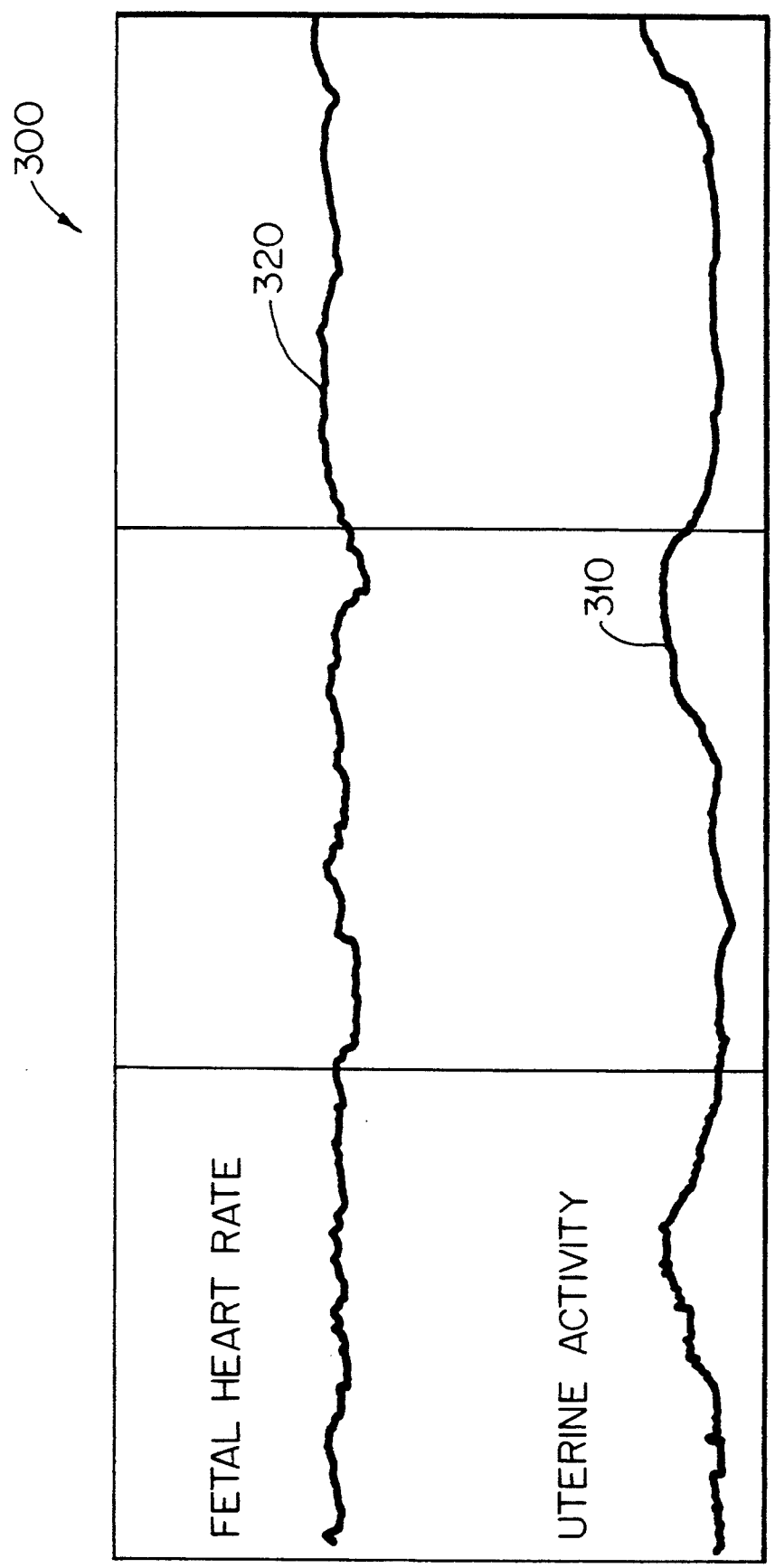
FIG. 3 shows typical strip recording of the uterine activity of an animal.

FIG. 3 shows an example of a strip chart 300 which may be obtained from monitoring the uterine activity of a horse. Strip chart 300 includes a trace 310 for uterine activity as well as a trace 320 for fetal heart rate, which is an optional measurement.

Preferably, the caregiver should record data at least once daily for 30 minutes. More frequent or longer monitoring sessions may be performed based on the animal's individual needs.

Figure 4:
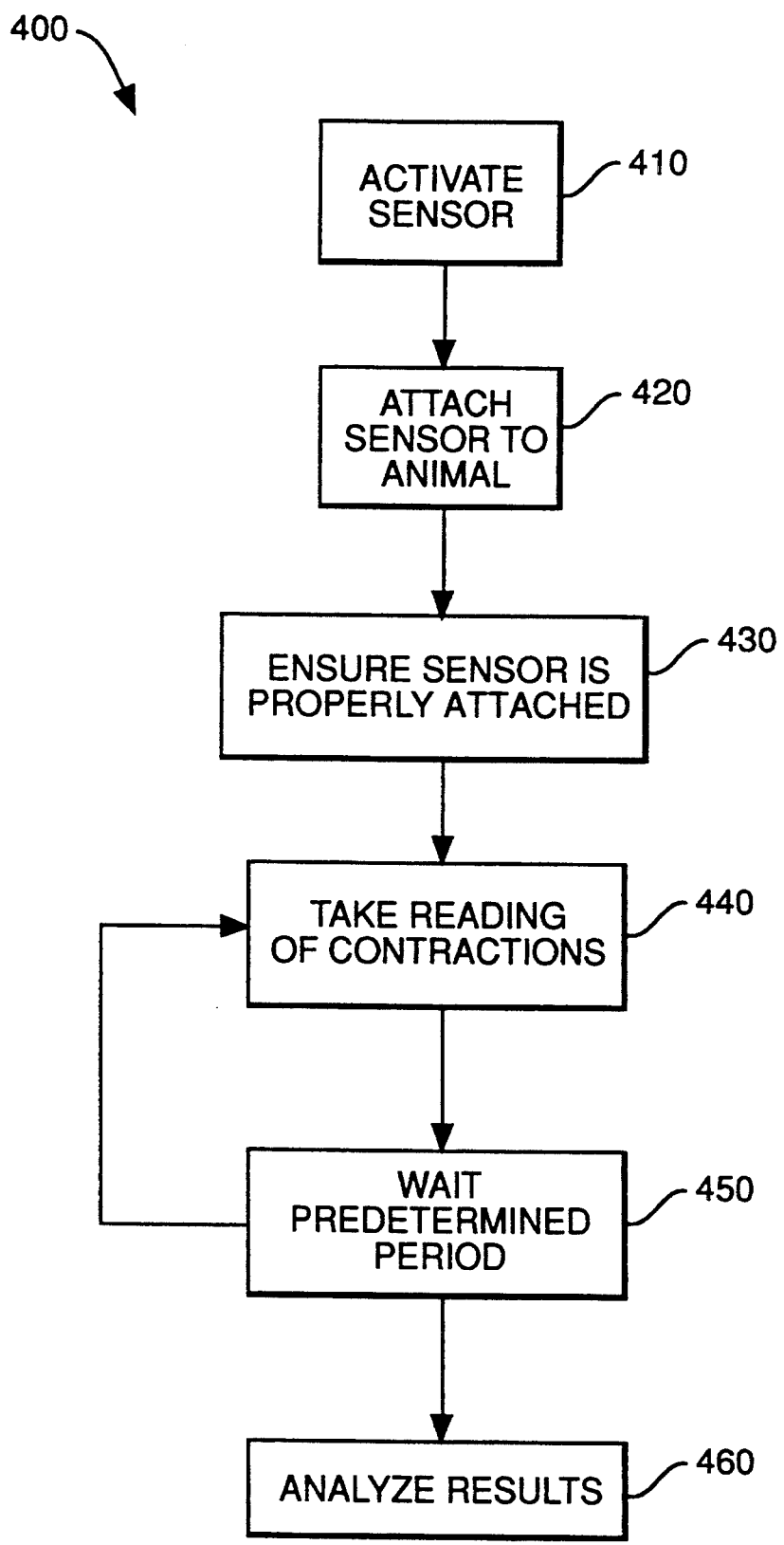
FIG. 4 is a flow diagram of the steps performed during monitoring.

FIG. 4 shows a detailed flow diagram 400 of the steps involved in monitoring the uterine activities of animals. First the sensor is activated (step 410), and then the belt with the sensor is attached to the animal and tightened around its abdomen (step 420). Checks are made to ensure that the sensor is properly attached (step 430), and then a reading is taken of the uterine contractions (step 440). Such readings, as mentioned above, take ½ to 1 hours. Readings are then taken periodically (step 450), and the data from such readings is analyzed at the appropriate facility (step 460).

Use of this method will enable the practitioner access to data on an as needed basis without having to travel to the site unless the data or symptoms warrant a physical assessment. It may allow practitioners to care for several animals at one time, and will allow the owner or caretaker to be a more active participant in the care of their animal's pregnancy and management of labor and delivery.

This technology will also enable an owner or caretaker trained in the simple use of the equipment to record this data and send it to a practitioner for interpretation at another location. Such data will provide pertinent information to a veterinarian concerning the prenatal condition of the animal, and will be helpful in documenting uterine activity.

What is claimed is:

1. A method of monitoring uterine activity in a non-human mammal comprising the steps of:
    noninvasively positioning on the mammal a pressure-sensitive sensor for detecting uterine contractions in the mammal, the position of the sensor being chosen on the mammal where the uterine contractions may be externally sensed
    connecting the sensor to an electronic device for recording the uterine contractions of the mammal; and
    periodically recording the uterine contractions of the mammal using the electronic device.

2. The method of claim 1 further including the step of transmitting the recorded uterine contractions of the mammal to a remote location.

3. The method of claim 1 wherein the step of recording the uterine contractions of the mammal includes the step of
    making a strip chart recording of the uterine contractions of the mammal.

4. The method of claim 1 wherein the step of connecting the sensor to the electronic device includes the step of using a cord.

5. The method of claim 1 wherein the step of connecting the sensor to the electronic device includes the step of establishing a cordless communications path.

6. A method of monitoring uterine contractions of a plurality of non-human mammals comprising the steps of:
    noninvasively positioning on each of the plurality of mammals a pressure-sensitive sensor for detecting uterine contractions of mammals, the positions of the sensors being chosen on the mammals where the uterine contractions may be externally sensed;
    connecting the sensors to an electronic device for recording the uterine contractions of the mammals; and
    periodically recording the uterine contractions of the mammals using the electronic device.

* * * * *